United States Patent
Kim et al.

(10) Patent No.: US 7,935,519 B2
(45) Date of Patent: May 3, 2011

(54) DNA CHIP, DNA CHIP KIT, AND METHOD OF MANUFACTURING THE DNA CHIP

(75) Inventors: Won-sun Kim, Suwon-si (KR);
Sung-min Chi, Hwaseong-si (KR);
Jung-hwan Hah, Hwaseong-si (KR);
Kyoung-seon Kim, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 1042 days.

(21) Appl. No.: 11/790,351

(22) Filed: Apr. 25, 2007

(65) Prior Publication Data

US 2007/0259418 A1  Nov. 8, 2007

(30) Foreign Application Priority Data

May 2, 2006 (KR) .................. 10-2006-0039703

(51) Int. Cl.
*C12M 1/34* (2006.01)
*C12Q 1/68* (2006.01)

(52) U.S. Cl. ........ 435/287.2; 435/6; 435/288.7; 257/40; 313/504; 977/704; 977/792; 977/924

(58) Field of Classification Search ........................ None
See application file for complete search history.

(56) References Cited

U.S. PATENT DOCUMENTS

| | | | |
|---|---|---|---|
| 2002/0106682 A1 | 8/2002 | Lee et al. | |
| 2002/0137066 A1* | 9/2002 | Kajiyama et al. | 435/6 |
| 2003/0181694 A1* | 9/2003 | Shirane et al. | 536/23.1 |
| 2006/0194228 A1* | 8/2006 | Rakitin et al. | 435/6 |

FOREIGN PATENT DOCUMENTS

| | | |
|---|---|---|
| KR | 10-2002-0064805 | 8/2002 |
| KR | 10-2004-0085485 | 10/2004 |
| KR | 10-2005-0017441 | 2/2005 |

* cited by examiner

*Primary Examiner* — William H Beisner
(74) *Attorney, Agent, or Firm* — Cantor Colburn LLP

(57) ABSTRACT

A DNA chip includes a substrate, at least one first electrode and at least one second electrode on the substrate, the first electrode and the second electrode being opposite to and separated from each other, multiple oligonucleotide probes, one end of the oligonucleotide probes being immobilized on the first electrode, and a charge-carrier transport layer on the second electrode, the charge-carrier layer contacting an other end of the oligonucleotide probes.

21 Claims, 17 Drawing Sheets

United States Patent US 7,935,519 B2

DNA CHIP, DNA CHIP KIT, AND METHOD OF MANUFACTURING THE DNA CHIP

BACKGROUND OF THE INVENTION

1. Field of the Invention

The present invention relates to a DNA chip, more particularly, to a DNA chip achieving precise DNA analysis, a DNA chip kit, and a method of manufacturing the DNA chip.

2. Description of the Related Art

Biochips may be biological microchips in which biomolecules, e.g., DNAs, proteins, etc., may be immobilized on small substrates and may be used to analyze genetic defects, protein distribution, reaction patterns, etc. In recent years, with the advance of genome projects, the genomic nucleotide sequences of various organisms have been identified. Thus, there has been an increasing interest in microchips, i.e., DNA microchips, for analyzing the DNA of an organism.

DNA microchips may be immobilized with multiple single-stranded cDNA probes or oligonucleotide probes. The type and quantity of probes to be immobilized may be changed according to the specific application of the DNA microchips.

When target analytes labeled with a labeling agent, e.g., a fluorescent substance, etc., are applied to DNA chips, complementary hybridization may occur. Once hybridization is accomplished, the labeling agent may be left on the DNA microchips even after the DNA microchips are washed. Thus, when the DNA microchips are exposed to light, fluorescent light having a predetermined wavelength may be emitted from the labeling agent of the DNA chips. The emitted fluorescent light may be analyzed by a photodetector to determine the occurrence and degree of hybridization.

However, when the DNA chips are exposed to light after hybridization, an excitation light for exciting the labeling agent may be diffusedly reflected from the chip substrates, or any light that does not contribute to the excitation of the labeling agent may be reflected from the chip substrates, thereby resulting in an interference between the reflected light and normal fluorescent light. The light interference may appear as signal noise, i.e., a reduced intensity of fluorescent light emission, which may make it difficult to achieve precise DNA analysis, thereby leading to a reduction in the reliability of the DNA analysis.

SUMMARY OF THE INVENTION

The present invention is therefore directed to a DNA chip and a DNA chip kit that substantially overcomes one or more of the problems due to the limitations and disadvantages of the related art.

It is therefore a feature of an embodiment of the present invention to provide a DNA chip and a DNA chip kit that may achieve precise DNA analysis, and a method of manufacturing a DNA chip.

At least one of the above and other features and advantages of the present invention may be realized by providing a DNA chip that may include a substrate, at least one first electrode and at least one second electrode that may be on the substrate, the first electrode and the second electrode being opposite to and separate from each other, multiple oligonucleotide probes, where one end of the oligonucleotide probes may be immobilized on the first electrode, and a charge-carrier transport layer may be on the second electrode, the charge carrier layer contacting an other end of the oligonucleotide probes.

At least one of the above and other features and advantages of the present invention may be realized by providing a DNA chip that may include a first substrate having a first electrode and multiple oligonucleotide probes, where one end of the oligonucleotide probes may be immobilized on the first electrode, and a second substrate that may have a second electrode and a charge-carrier transport layer, the first substrate and the second substrate being opposite to each other so that the charge-carrier transport layer may contact an other end of the oligonucleotide probes.

At least one of the above and other features and advantages of the present invention may be realized by providing a DNA chip kit that may include a first unit including a first substrate having a first electrode on the first substrate, and multiple oligonucleotide probes, where one end of the oligonucleotide probes may be immobilized on the first electrode, and a second unit may include a second substrate, a second electrode that may be on the second substrate, and a charge-carrier transport layer that may be on the second electrode, the charge-carrier transport layer being capable of contacting an other end of the oligonucleotide probes.

At least one of the above and other features and advantages of the present invention may be realized by providing a method of manufacturing a DNA chip, including forming at least one first electrode and at least one second electrode that may be on at least one substrate, the first electrode and the second electrode being opposite to and separated from each other, forming a charge-carrier transport layer that may be on the second electrode, and immobilizing multiple oligonucleotide probes on the first electrode, where one end of the oligonucleotide probes may contact the first electrode and the other end of the oligonucleotide probes may contact the charge-carrier transport layer.

BRIEF DESCRIPTION OF THE DRAWINGS

The above and other features and advantages of the present invention will become more apparent to those of ordinary skill in the art by describing in detail exemplary embodiments thereof with reference to the attached drawings, in which.

DETAILED DESCRIPTION OF THE INVENTION

Figure 1:
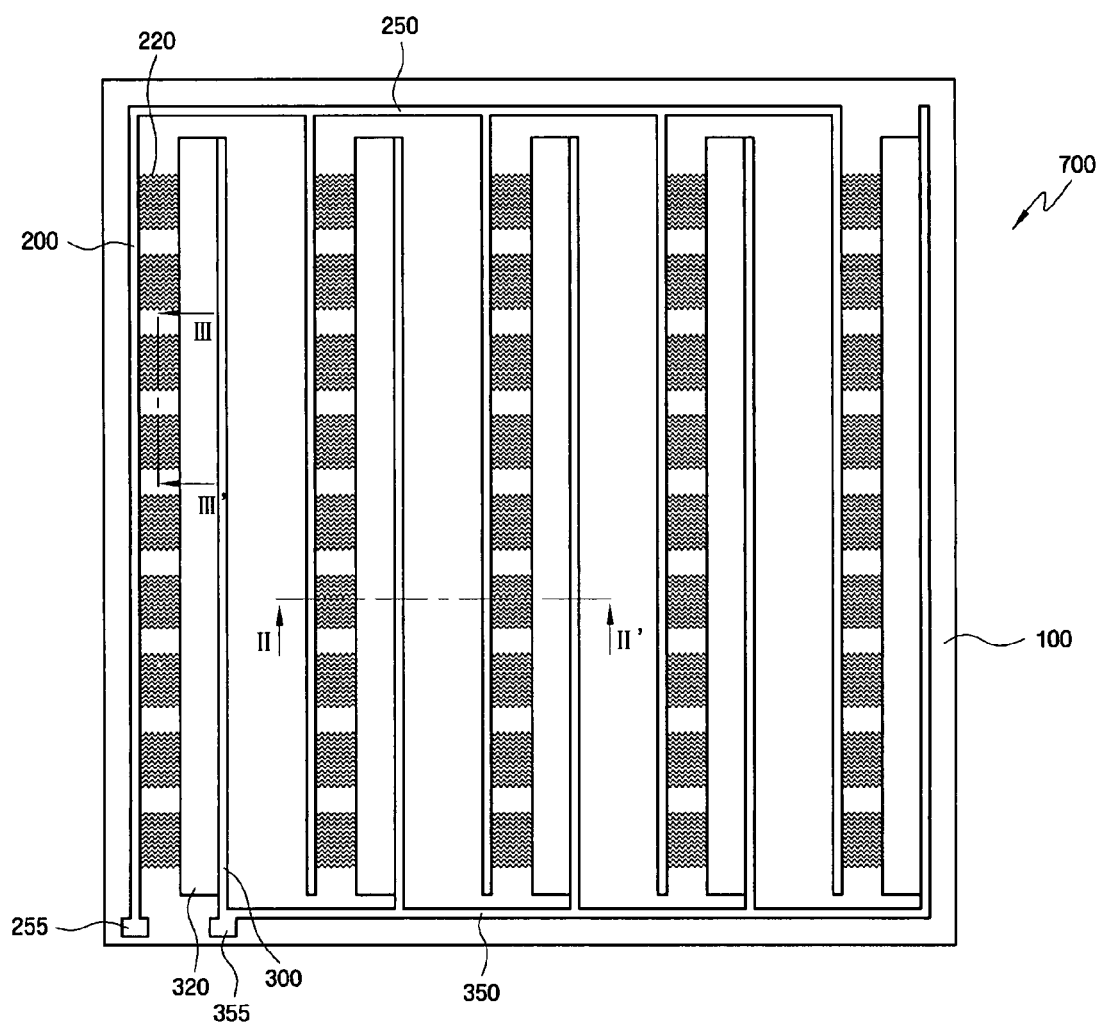
FIG. 1 illustrates a plan view of a DNA chip according to a first embodiment of the present invention.

Korean Patent Application No. 10-2006-0039703, filed on May 2, 2006, in the Korean Intellectual Property Office, and entitled: "DNA Chip, DNA Chip Kit, and Method of Manufacturing the DNA Chip," is incorporated by reference herein in its entirety.

The present invention will now be described more fully hereinafter with reference to the accompanying drawings, in which exemplary embodiments of the invention are illustrated. The invention may, however, be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

Spatially relative terms, such as "beneath", "below", "lower", "above", "upper" and the like, may be used herein for ease of description to describe one element or feature's relationship to another element(s) or feature(s) as illustrated in the drawing figures. It will be understood that the spatially relative terms are intended to encompass different orientations of the element or feature in use or operation in addition to the orientation depicted in the drawing figures.

A DNA chip according to the present invention will now be described more fully with reference to the accompanying drawings, in which exemplary embodiments of the invention are shown.

Figure 2:
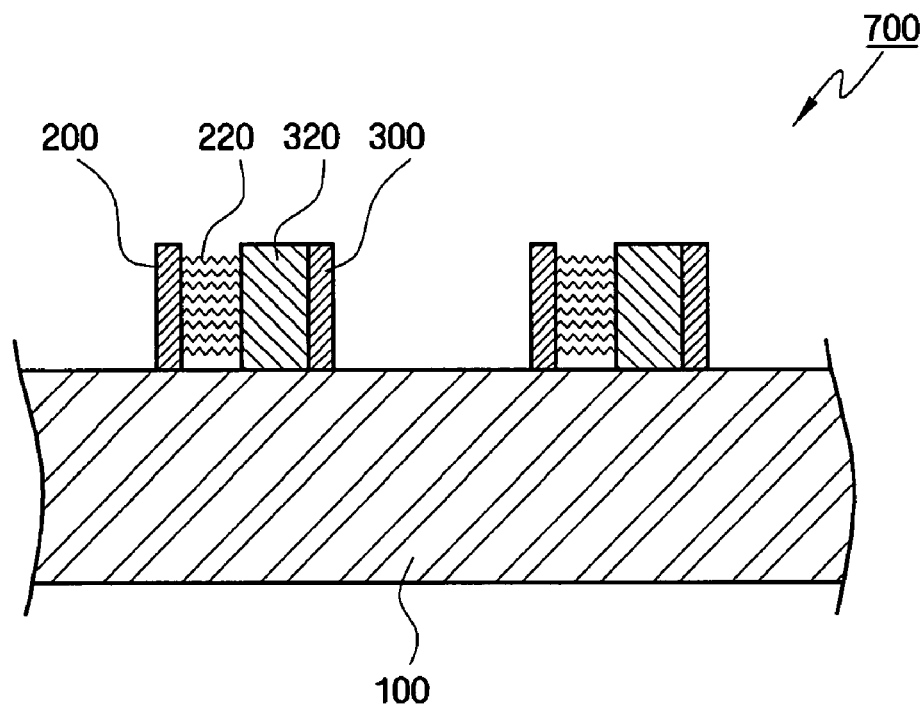
FIG. 2 illustrates a sectional view taken along a line II-II' of FIG. 1.
Figure 3:
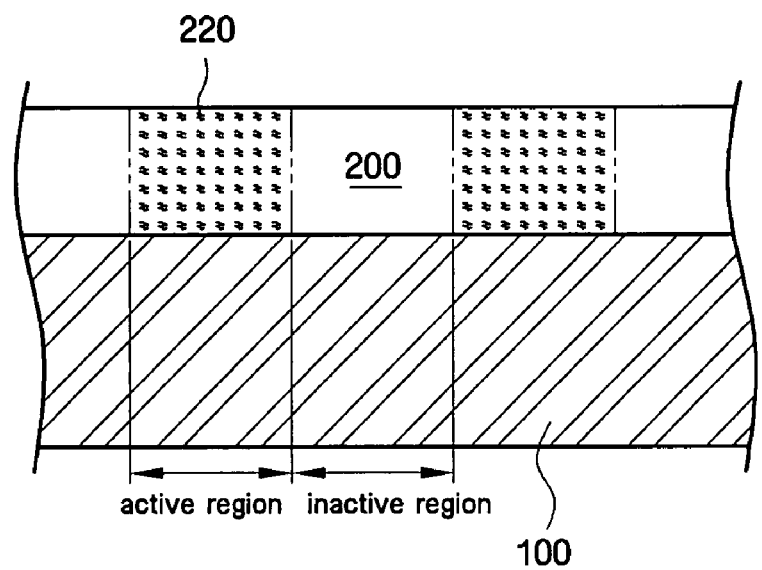
FIG. 3 illustrates a sectional view taken along a line III-III' of FIG. 1.

FIG. 1 illustrates a plan view of a DNA chip according to a first embodiment of the present invention, FIG. 2 illustrates a sectional view taken along a line II-II' of FIG. 1, and FIG. 3 illustrates a sectional view taken along a line III-III' of FIG. 1.

Referring to FIGS. 1 through 3, a DNA chip 700 according to a first embodiment of the present invention may include multiple first electrodes 200 and multiple second electrodes 300 on a substrate 100, multiple oligonucleotide probes 220 that may be immobilized on the first electrodes 200, and charge-carrier transport layers 320 that may be on the second electrodes 300.

The substrate 100 may provide a place for the formation of the first and second electrodes 200 and 300, and the substrate 100 may support the first and second electrodes 200 and 300. The size of the substrate 100 may be widely modified according to the types and number of the oligonucleotide probes 220. The substrate 100 may be, e.g., square, rectangular, circular, etc., but is not limited thereto. The substrate 100 may have no limitations provided that it may support the first electrodes 200, the second electrodes 300, etc. Preferably, the substrate 100 may be a material selected from, e.g., glass, silicone, fused silica, polystyrene, polymethylacrylate, polycarbonate, gold, silver, copper, platinum, palladium, etc.

The first electrodes 200 and the second electrodes 300 may alternate with each other on the substrate 100. The first electrodes 200 may extend in a first direction (a vertical direction in FIG. 1). Although FIG. 1 illustrates that the multiple first electrodes 200 may be arranged in parallel and separated from each other by a predetermined distance in order to define multiple active regions, a single first electrode may also be disposed on the substrate 100. The first electrodes 200 may be electrically connected to each other by first connection electrodes 250 extending in a second direction (a horizontal direction in FIG. 1) at a side of the substrate 100. First electrode pads 255 receiving an external voltage may be disposed on edge portions of the first electrodes 200 or the first connection electrodes 250. The same voltage may be applied to the first electrodes 200 through the first electrode pads 255 and the first connection electrodes 250. The first electrodes 200 may be made of, e.g., copper, silver, aluminum, gold, indium, calcium, ITO (Indium Tin Oxide), IZO (Indium Zinc Oxide), etc. The first electrodes 200, when used as cathodes, may be made of a material with a low work function, e.g., copper, silver, aluminum, gold, indium, calcium, etc.

The second electrodes 300 may extend in the first direction, like the first electrodes 200. The number of the second electrodes 300 may be the same as the number of the first electrodes 200. The second electrodes 300 may be paired with the first electrodes 200 to generate an electric field in active regions. The second electrodes 300 may be arranged in parallel and separated from each other by a predetermined distance. The second electrodes 300 may be electrically connected to each other by second connection electrodes 350 extending in the second direction at the side of the substrate 100 opposite to the first connection electrodes 250. Second electrode pads 355 receiving an external voltage may be disposed on edge portions of the second electrodes 300 or the second connection electrodes 350. The same or a different voltage may be applied to the second electrodes 300 through the second electrode pads 355 and the second connection electrodes 350. The second electrodes 300 may be made of, e.g., copper, silver, aluminum, gold, indium, calcium, ITO, IZO, etc. The second electrodes 300, when used as anodes, may be made of a material with a high work function, e.g., ITO, IZO, etc.

Reactive functional groups capable of reacting with monomers for oligonucleotide synthesis may be present on a sidewall surface of each of the first electrodes 200 or on portions of the sidewall surface corresponding to active regions. The reactive functional groups may be derived from linkers (not shown) coated on the surfaces of the first electrodes 200. Alternatively, the reactive functional groups may also be derived from, i.e., directly attached to, the surfaces of the first electrodes 200, i.e., the material constituting the first electrodes 200. The reactive functional groups may be, e.g., hydroxyl groups, amino groups, thiol groups, aldehyde groups, carboxyl groups, acyl groups, etc. The oligonucleotide probes 220 may be immobilized on the first electrodes 200 by coupling the reactive functional groups with the oligonucleotide probes 220. Although active regions of the first electrodes 200 may have inactivated or acetyl-capped reactive functional groups, the inactivated or acetyl-capped reactive functional groups may not contribute to immobilization of the oligonucleotide probes 220.

An active region may be wholly formed along a sidewall of each of the first electrodes 200. However, multiple active regions may also be defined in a sidewall of each of the first electrodes 200, as illustrated in FIG. 3. Regions between adjacent two of active regions in a sidewall of each of the first electrodes 200 may be defined as inactive regions, i.e., isolation regions. The inactive regions may be regions that have no activated functional groups. The inactive regions may not have the above-illustrated reactive functional groups or may only have an inactivated or capped form of the reactive functional groups. The oligonucleotide probes 220 may thus not be immobilized in the inactive regions. The inactive regions of the first electrodes 200 may include reactive functional group-containing linkers, but the reactive functional groups may not be inactivated or capped.

The oligonucleotide probes 220 may be immobilized on the first electrodes 200 by coupling them with the reactive functional groups in the active regions. The oligonucleotide probes 220 may be single-stranded oligonucleotides capable of forming complementary base pairs with targets. For example, when single-stranded DNAs are used as targets whose DNA sequences may be unknown, the oligonucleotide probes 220 may be single-stranded oligonucleotides including a combination of adenine (A), guanine (G), thymine (T), and cytosine (C) monomers. The number of monomers constituting each of the oligonucleotide probes 220 may be, e.g., about 5 to 30, but the present invention is not limited thereto.

One of the ends of the multiple oligonucleotide probes 220 may be immobilized in each active region. About 500 to about 100,000 oligonucleotide probes 220 may be immobilized in each active region. All oligonucleotide probes 220 immobilized in an active region may have substantially the same nucleotide sequences. When needed, oligonucleotide probes 220 immobilized in an active region may have substantially the same nucleotide sequences, similar nucleotide sequences to (variation in one or two monomers), or different nucleotide sequences from oligonucleotide probes immobilized in another active region.

The charge-carrier transport layers 320 may be disposed on one of the sidewalls of the second electrodes 300. When the second electrodes 300 are used as anodes, the charge-carrier transport layers 320 may be responsible for hole-carrier transport from the second electrodes 300. The charge-carrier transport layers 320 may be made of, e.g., poly(9-vinylcarbazole), polycarbonate, poly(phenylenevinylene), etc.

The charge-carrier transport layers 320 may be disposed on the sidewalls of the second electrodes 300 facing with the first electrodes 200. The charge-carrier transport layers 320 may be disposed on the entire surfaces of the sidewalls of the second electrodes 300 facing with the first electrodes 200 irrespective of the active regions of the first electrodes 200, including the reactive functional groups.

The charge-carrier transport layers 320 may contact with or may be adjacent to the distal ends of the oligonucleotide probes 220 from the first electrodes 200. That is, gaps between the first electrodes 200 and the charge-carrier transport layers 320 may be smaller than or be the same as the lengths of the oligonucleotide probes 220, so that the distal ends of the oligonucleotide probes 220 from the first electrodes 200 may contact the charge-carrier transport layers 320. Alternatively, the gaps between the first electrodes 200 and the charge-carrier transport layers 320 may be greater than the lengths of the oligonucleotide probes 220 so that the distal ends of the oligonucleotide probes 220 from the first electrodes 200 may be adjacent to the charge-carrier transport layers 320. In the latter case, gaps between the distal ends of the oligonucleotide probes 220 from the first electrodes 200 and the charge-carrier transport layers 320 may be adjusted at least so that, when the oligonucleotide probes 220 are hybridized with targets containing an organic light-emitting material, the organic light-emitting material may contact with the charge-carrier transport layers 320.

The above-described DNA chip may be used in analysis of target DNAs. Hereafter, a method of analyzing target DNAs using the DNA chip according to the first embodiment of the present invention will be described with reference to FIGS. 4 and 5.

Figure 4:
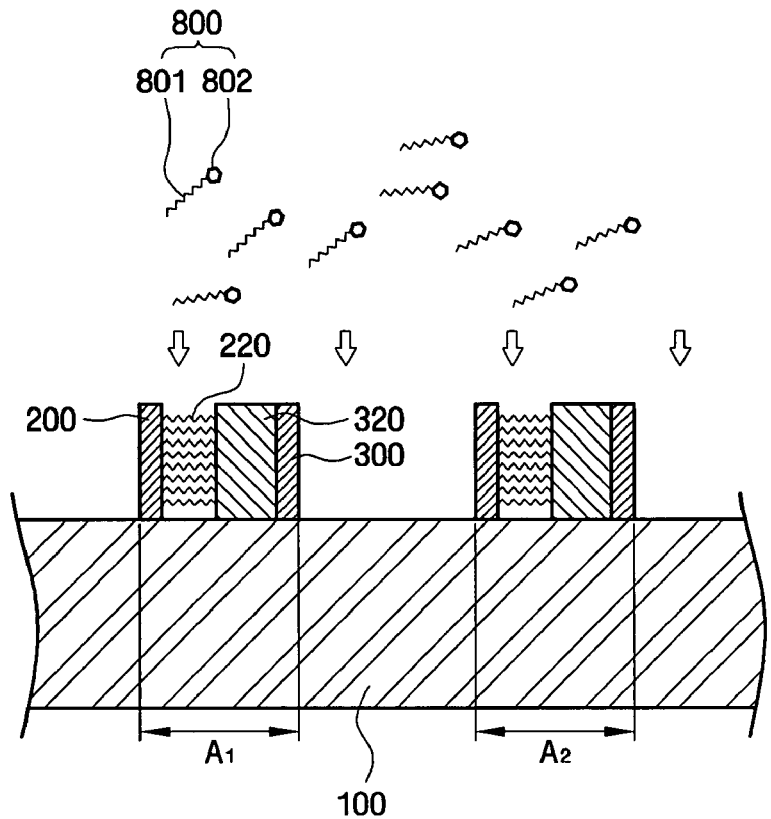
FIGS. 4 and 5 illustrate sectional views of a DNA analysis using the DNA chip according to the first embodiment of the present invention.
Figure 5:
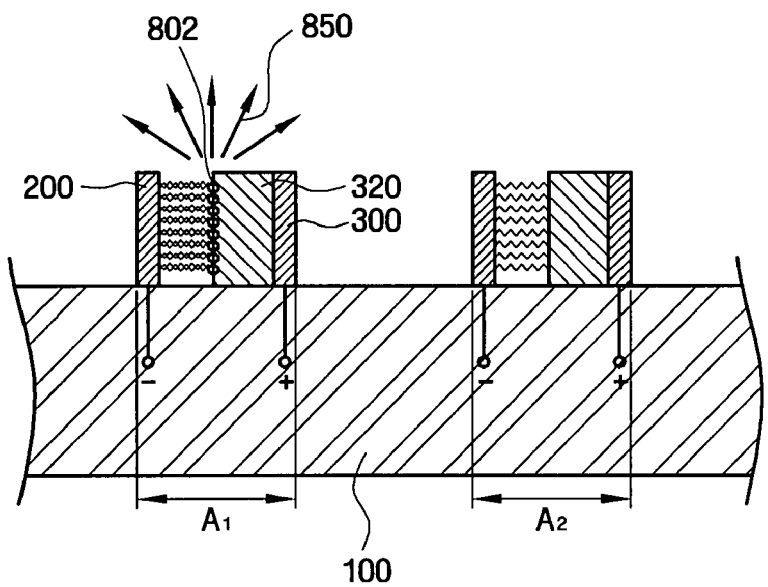

FIGS. 4 and 5 illustrate sectional views of stages of a DNA analysis using the DNA chip according to the first embodiment of the present invention.

Referring to FIG. 4, a DNA chip is prepared which has oligonucleotide probes 220 that may be immobilized in a first region $A_1$, and other oligonucleotide probes 220 may be immobilized in a second region $A_2$. Then, targets 800 may be prepared where organic light-emitting materials 802 may be attached to ends of single-stranded DNAs 801. The organic light-emitting materials 802 may be organic single-molecules, e.g., aluminaquinone, anthracene, cyclopentadiene derivatives, perylene, etc. The organic light-emitting materials 802 may also be polymers, e.g., poly(phenylenevinylene), poly(p-phenylene), polythiophene, derivatives thereof, etc.

When 3'-ends of the oligonucleotide probes 220 may be bound to first electrodes 200, the organic light-emitting materials 802 may be attached to 3'-ends of the single-stranded DNAs 801 of the targets 800 since the organic light-emitting materials 802 may be bound to the 5'-ends of the oligonucleotide probes 220 during hybridization.

Next, the targets 800 attached with the organic light-emitting materials 802 may be supplied to the DNA chip. The DNA chip may be washed a predetermined time after the targets 800 have been supplied.

Referring to FIG. 5, together with FIG. 4, the targets 800 attached to the organic light-emitting materials 802 may be complementarily hybridized with the oligonucleotide probes 220 on the DNA chip. If the nucleotide sequences of the oligonucleotide probes 220 in the first region $A_1$ match with the nucleotide sequences of the single-stranded DNAs 801 of the targets 800, target-probe hybridization may occur in the first region $A_1$. On the other hand, target-probe hybridization may not occur in the second region $A_2$ because the nucleotide sequences of the single-stranded DNAs 801 of the targets 800 may be mismatched with the oligonucleotide probes 220 in the second region $A_2$. Thus, the single strands of the oligonucleotide probes 220 may remain unreacted. In the first region $A_1$, the organic light-emitting materials 802 of the targets 800 hybridized with the oligonucleotide probes 220 may contact with surfaces of charge-carrier transport layers 320. Target-probe hybrids may hang down so as not to contact with the charge-carrier transport layers 320. In order to prevent this phenomenon, a buffer may be supplied.

The target-probe hybrids in the first region $A_1$ may have electron transport capability due to high electroconductivity. When a negative voltage and a positive voltage are respectively applied to the first electrodes 200 and second electrodes 300, electrons from the first electrodes 200 may be transported to the organic light-emitting materials 802 along the target-probe hybrids. At the same time, holes from the second electrodes 300 may be transported to the organic light-emitting materials 802 along the charge-carrier transport layers 320. The electrons and the holes may be combined in the organic light-emitting materials 802, thereby emitting light beams 850.

The oligonucleotide probes 220 in the second region $A_2$ may have little or no electroconductivity, i.e., little or no electron transport capability. Thus, even when a negative voltage and a positive voltage are respectively applied to the first electrodes 200 and the second electrodes 300, electron transport to the organic light-emitting materials 802 from the first electrodes 200 may hardly occur. Thus, light emission may not occur in the second region $A_2$.

Light emission may be detected visually or with the aid of a photodetector, e.g., a Charge-Coupled Device (CCD), a CMOS Image Sensor (CIS), etc. From the detection results of the light emission, it may be determined if the single-stranded target DNAs are complementary to the oligonucleotide probes 220.

In the DNA chip according to the first embodiment of the present invention, target-probe hybridization may be detected by light emitted from an organic light-emitting material. Noise due to external light or reflected light may not occur, thereby allowing a more precise DNA analysis.

Hereafter, a method of manufacturing the DNA chip according to the first embodiment of the present invention will be described with reference to FIGS. 6 through 8.

Figure 6:
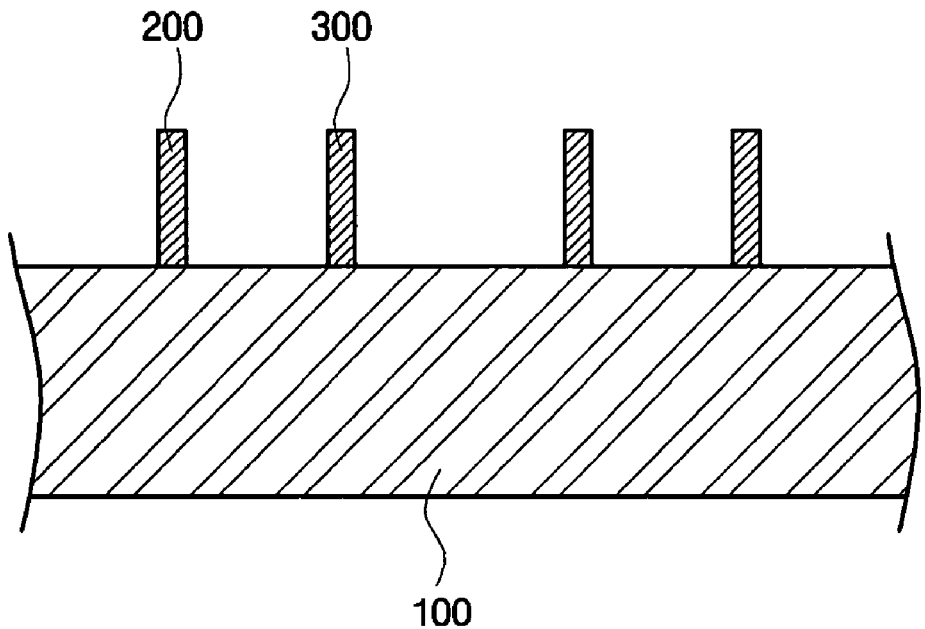
FIGS. 6 through 8 illustrate sequential sectional views of stages of a method of manufacturing the DNA chip according to the first embodiment of the present invention.
Figure 7:
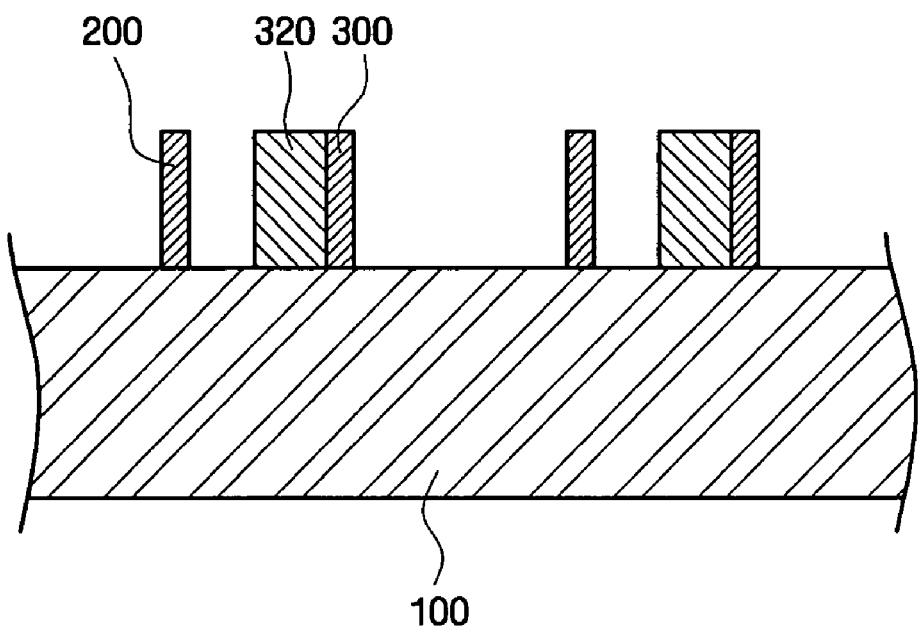
Figure 8:
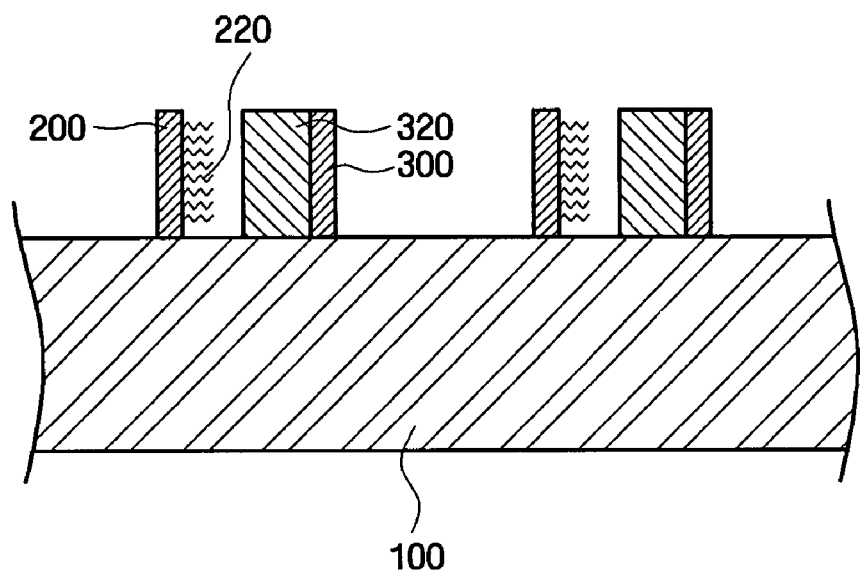

FIGS. 6 through 8 illustrate sequential sectional views of stages of a method of manufacturing the DNA chip according to the first embodiment of the present invention.

First, referring to FIG. 6, a first electrode 200 and a second electrode 300 may be formed on a substrate 100. If the first electrode 200 and the second electrode 300 are formed using different materials, a first electrode material may be deposited on the substrate 100 by, e.g., sputtering, and patterned by, e.g., photolithography. Then, a second electrode material may be deposited on the substrate 100 by, e.g., sputtering and patterned by, e.g., photolithography. The second electrode 300 may also be formed prior to forming the first electrode 200.

Next, active regions may be defined in a sidewall of the first electrode 100 facing the second electrode 300. For example, when the first electrode 200 includes surface reactive functional groups capable of reacting with monomers for oligonucleotide synthesis, reactive functional groups in first electrode regions except the active regions may be inactivated or capped. When the first electrode 200 is coated with linkers, reactive functional groups may be present only in first electrode regions intended for the active regions. The reactive functional groups in the active regions may also be protected with photo-labile protecting groups.

Next, referring to FIG. 7, together with FIG. 6, a charge-carrier transport layer 320 may be formed on a sidewall of the second electrode 300 facing with the first electrode 200. A material, e.g., poly(9-vinylcarbazole), polycarbonate, poly (phenylenevinylene), etc., may be deposited on the resultant structure of FIG. 6, and patterned by, e.g., photolithography. This process may also be performed prior to defining the active regions.

Next, referring to FIG. 8, together with FIG. 7, oligonucleotide monomers may be sequentially attached to the active regions defined in the first electrode 200 to synthesize oligonucleotide polymers. In detail, the protecting groups attached to the reactive functional groups may be selectively removed from predetermined active regions using a mask to activate the reactive functional groups, and first oligonucleotide monomers having reactive functional groups capable of coupling with the activated functional groups may be introduced to the predetermined active regions so that the first oligonucleotide monomers may be immobilized in the predetermined active regions. Then, protecting group-protected reactive functional groups of the previously attached first oligonucleotide monomers may be selectively exposed to light using a mask to activate the reactive functional groups, and second oligonucleotide monomers having reactive functional groups capable of coupling with the activated functional groups may be introduced to the predetermined active regions. As a result, the second oligonucleotide monomers may be coupled to the predetermined active regions. Repetition of the above-described processes may allow the synthesis of oligonucleotide probes 220 having a desired length and a combination of desired oligonucleotide monomers. This process may complete the DNA chip illustrated in FIG. 2.

Hereafter, DNA chips according to second through eighth embodiments of the present invention will be described with reference to FIGS. 9 through 15. In the following embodiments of the present invention, a description of similar constitutional elements as those in the previous embodiment will be omitted or simply described, and constitutional elements different from those in the previous embodiment will be described in detail.

Figure 9:
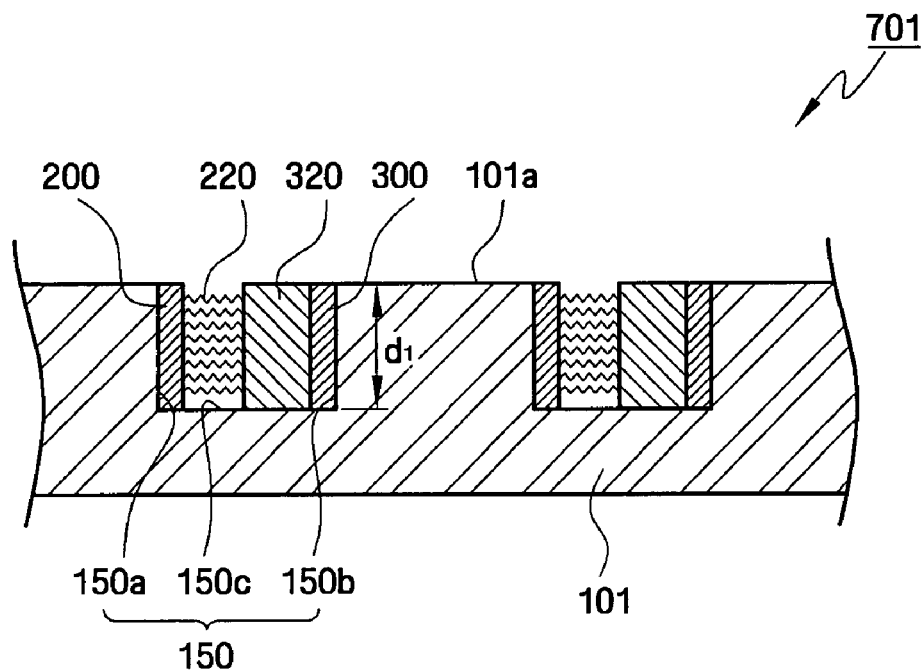
FIG. 9 illustrates a sectional view of a DNA chip according to a second embodiment of the present invention.

FIG. 9 illustrates a sectional view of a DNA chip according to a second embodiment of the present invention.

Referring to FIG. 9, a DNA chip 701 may include a substrate 101 that may have at least one trench 150. A first electrode 200 and a second electrode 300 may be formed in the trench 150, unlike the first embodiment illustrated in FIG. 2.

The substrate 101 may include the at least one trench 150 being depressed from an upper surface 101a of the substrate 101. The trench 150 may include a bottom 150c and first and second sidewalls 150a and 150b standing approximately vertical with respect to the bottom 150c. The first electrode 200 may be formed on the first sidewall 150a of the trench 150, and the second electrode 300 may be formed on the second sidewall 150b opposite to the first sidewall 150a. Oligonucleotide probes 220 may be immobilized on a sidewall of the first electrode 200, and the oligonucleotide probes 220 may be contacted to a surface of a charge-carrier transport layer 320 formed on a sidewall of the second electrode 300.

The shape and number of the trenches 150 formed in the substrate 101 may have no particular limitations. There may be no limitations to the shape of the first electrode 200 formed in the trench 150 and the number of active regions. When the first and second sidewalls 150a and 150b of the trench 150 are substantially square, the first and second sidewalls 150a and 150b of the trench 150 may be wholly covered with the first electrode 200, and a sidewall of the first electrode 200 may act as an active region for immobilization of the oligonucleotide probes 220. When the first and second sidewalls 150a and 150b of the trench 150 are rectangular (long width, short height), the first and second sidewalls 150a and 150b of the trench 150 may be wholly covered with the first electrode 200, and a sidewall of the first electrode 200 may be defined into multiple regions, i.e., active regions and inactive regions. In this case, the first electrode 200 may also be patterned into multiple first electrode regions.

According to the DNA chip 701 of the second embodiment of the present invention, a first electrode 200 and a second electrode 300 may be respectively formed on both sidewalls of a trench 150. Thus, even though the heights $d_1$ of the first and second electrodes 200 and 300 may be greater than the widths, the DNA chip 701 may have a stable structure.

A method of manufacturing the DNA chip according to the second embodiment of the present invention may be similar to the method of manufacturing the DNA chip according to the first embodiment of the present invention except that a trench 150 is formed in a substrate 101. The trench 150 may be formed using various methods known in the art.

Figure 10:
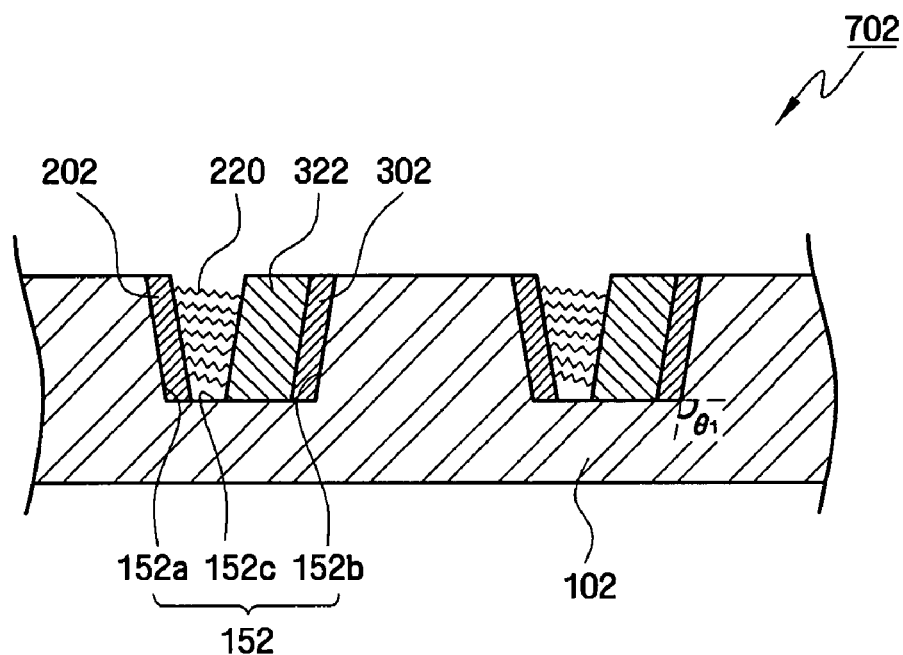
FIG. 10 illustrates a sectional view of a DNA chip according to a third embodiment of the present invention.

FIG. 10 illustrates a sectional view of a DNA chip 702 according to a third embodiment of the present invention. Referring to FIG. 10, a DNA chip 702 according to a third embodiment of the present invention differs from the DNA chip according to the second embodiment of the present invention in that a sidewall 152b of a trench 152 may be inclined at a predetermined angle $\theta_1$ with respect to a bottom 152c of the trench 152. Here, the angle $\theta_1$ may be greater than about 90 degrees, e.g., about 95-170 degrees. A second electrode 302 and a charge-carrier transport layer 322 formed on the sidewall of 152b of the trench 152 may be inclined at substantially the same angle as the angle $\theta_1$. The second electrode 302 and the charge-carrier transport layer 322 may have trapezoidal cross sections. As a result, a lower portion of the charge-carrier transport layer 322 may be positioned closer to a first electrode 202. Thus, even though oligonucleotide probes 220 grown horizontally with respect to the bottom 152c of the trench 152 hang down, in particular, if oligonucleotide probes 220 immobilized on an upper sidewall of the first electrode 202 hang down, they may contact the charge-carrier transport layer 322.

The opposite sidewall 152a to the sidewall 152b of the trench 150 may be inclined at the same angle as the sidewall 152b, but may alternately be vertical with respect to the bottom 152c of the trench 150. That is, there is no particular limitation to the inclination of the sidewall 152a of the trench 150.

Figure 11:
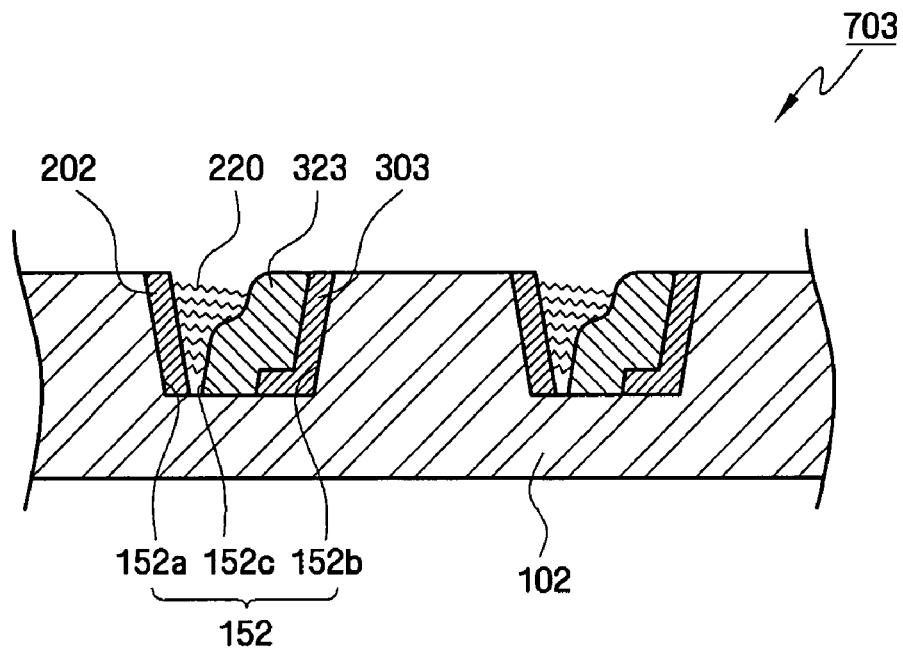
FIG. 11 illustrates a sectional view of a DNA chip according to a fourth embodiment of the present invention.

FIG. 11 illustrates a sectional view of a DNA chip according to a fourth embodiment of the present invention. Referring to FIG. 11, a DNA chip 703 according to a fourth embodiment of the present invention may include a trench 152 similar to the DNA chip of the third embodiment of the present invention, but a second electrode 303 and a charge-carrier transport layer 323 may extend to a bottom 152c from sidewall 152b of the trench 152. The second electrode 303 may be L-shaped. Therefore, even though oligonucleotide probes 220 hang down excessively, they may contact with the charge-carrier transport layer 323 formed on the bottom 152c, thereby ensuring contact between the oligonucleotide probes 220 and the charge-carrier transport layer 323.

Figure 12:
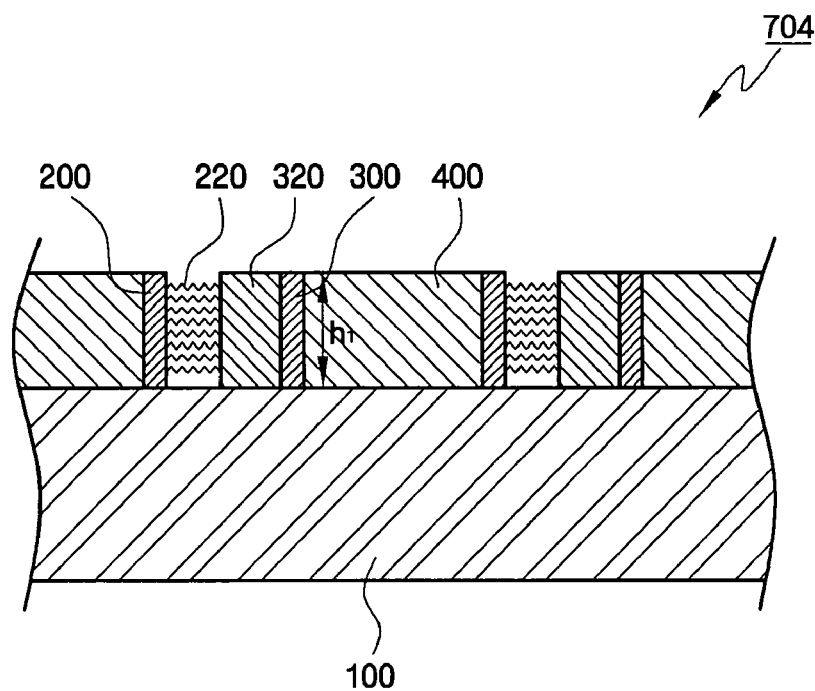
FIG. 12 illustrates a sectional view of a DNA chip according to a fifth embodiment of the present invention.

FIG. 12 illustrates a sectional view of a DNA chip according to a fifth embodiment of the present invention. Referring to FIG. 12, a DNA chip 704 may include a barrier rib pattern 400 that may be formed to a predetermined height $h_1$ on a substrate 100. Both sidewalls of the barrier rib pattern 400 may be respectively contacted to sidewalls, i.e., outer sidewalls, of first and second electrodes 200 and 300. A space defined by the barrier rib pattern 400 may substantially correspond to the trench (see 150 of FIG. 9) of the second embodiment of the present invention, and the space may contain the oligonucleotide probes 220 and the charge carrier transport layer 320. The shape of the barrier rib pattern 400 may be extensively changed to provide, e.g., the same shape and space as the trench of the second embodiment of the present invention. The barrier rib pattern 400 may serve to provide structural stability to the first electrode 200 and the second electrode 300 contacting with the sidewalls of the barrier rib pattern 400.

Figure 13:
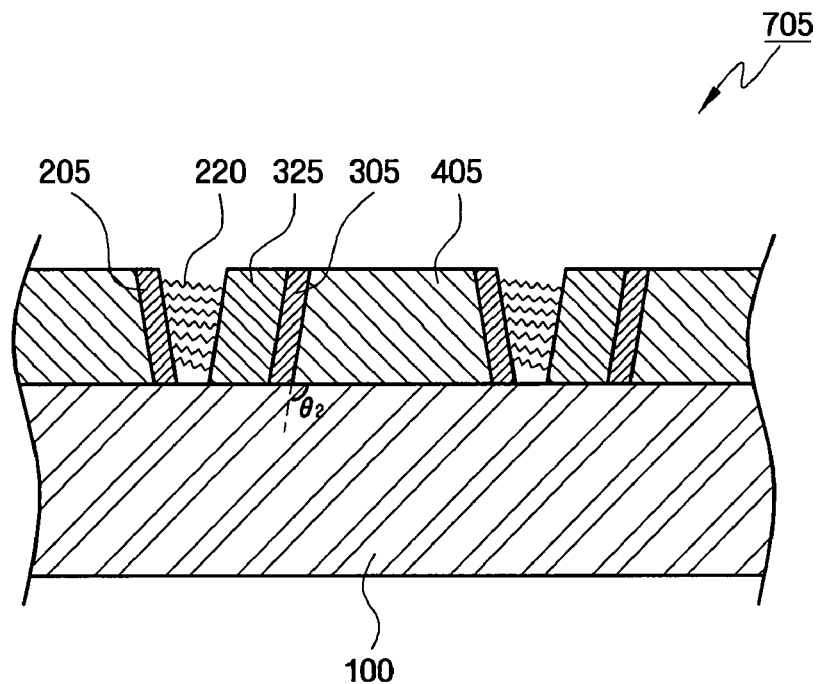
FIG. 13 illustrates a sectional view of a DNA chip according to a sixth embodiment of the present invention.

FIG. 13 illustrates a sectional view of a DNA chip according to a sixth embodiment of the present invention. Referring to FIG. 13, a DNA chip 705 may include a sidewall of a barrier rib pattern 405 inclined at a predetermined angle $\theta_2$ with respect to an upper surface of a substrate 100. In the current embodiment of the present invention, the shape of a space defined by the barrier rib pattern 405 may be substantially the same as that of the trench (see 152 of FIG. 10) of the third embodiment of the present invention. A second electrode 305 and a charge-carrier transport layer 325 formed on the sidewall of the barrier rib pattern 405 may be also inclined with respect to the upper surface of the substrate 100. A lower portion of the charge-carrier transport layer 325 may be positioned closer to a first electrode 205. Therefore, even though oligonucleotide probes 220 hang down, it may be possible to increase the probability of contact between the oligonucleotide probes 220 and the charge-carrier transport layer 325.

Figure 14:
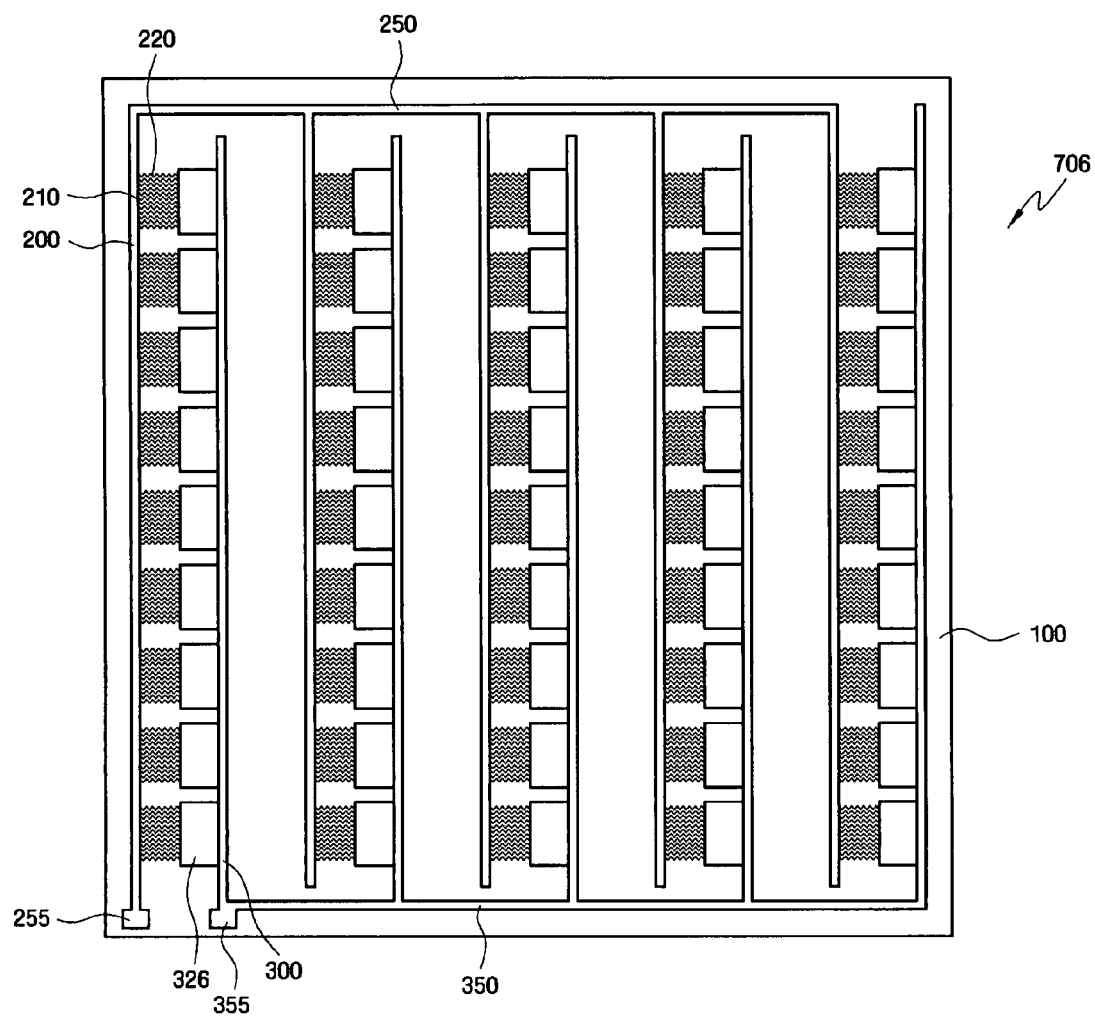
FIG. 14 illustrates a plan view of a DNA chip according to a seventh embodiment of the present invention.

FIG. 14 illustrates a plan view of a DNA chip according to a seventh embodiment of the present invention. Referring to FIG. 14, a DNA chip 706 may have substantially the same structure as the DNA chip of the first embodiment of the present invention illustrated in FIG. 1, except that a charge-carrier transport layer 326 may be formed to correspond to active regions immobilized by oligonucleotide probes 220. Thus, in DNA analysis using the DNA chip 706, it may be possible to prevent hole transport from the charge-carrier transport layer 326 to useless regions and to increase a hole density in the active regions.

Figure 15:
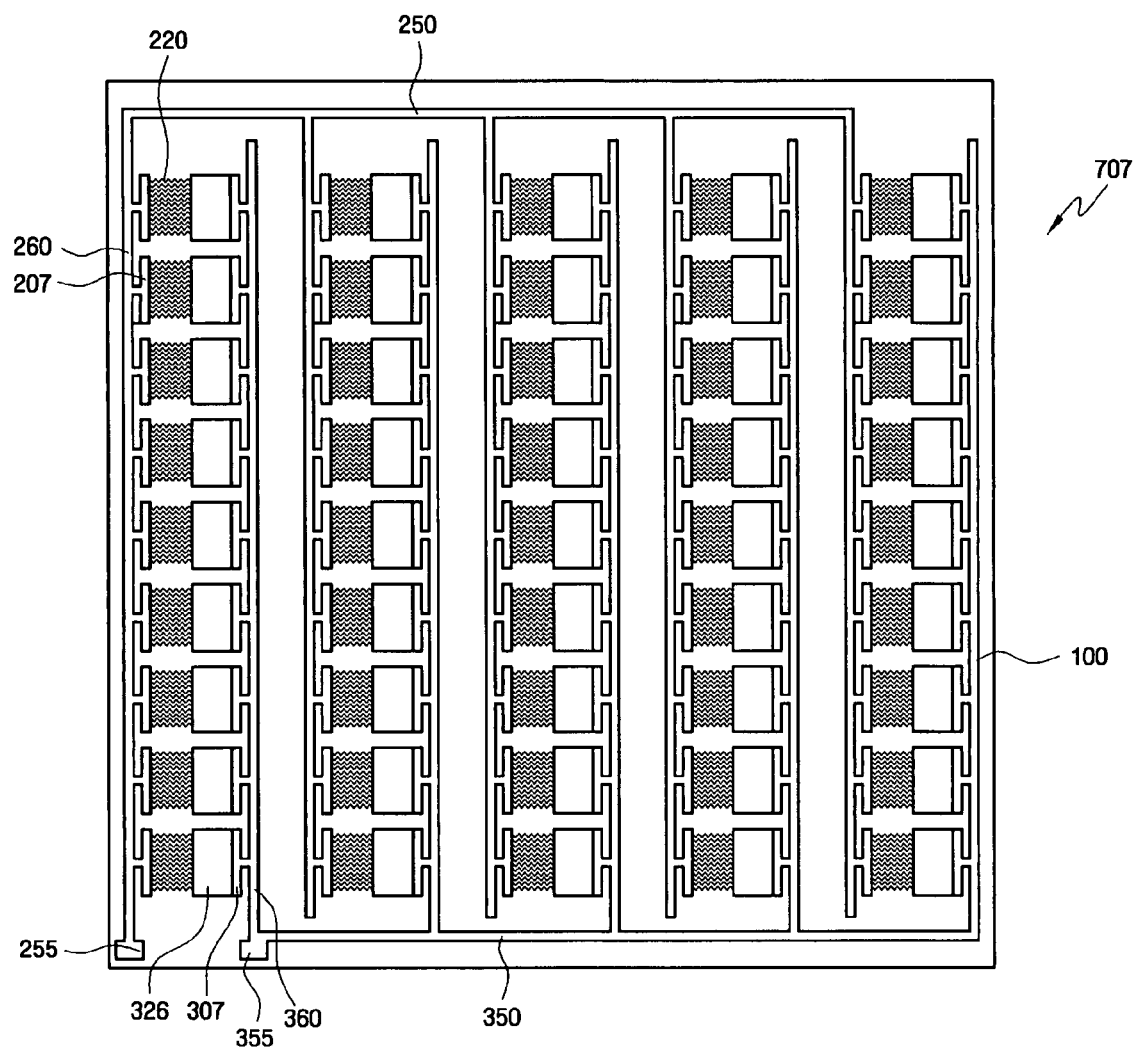
FIG. 15 illustrates a plan view of a DNA chip according to an eighth embodiment of the present invention.

FIG. 15 illustrates a plan view of a DNA chip according to an eighth embodiment of the present invention. Referring to FIG. 15, a DNA chip 707 may be structured such that a first electrode 207 and a second electrode 307, together with a charge-carrier transport layer 326, may be formed to correspond to active regions. The first electrode 207 and the second electrode 307 may have separate sections corresponding to active regions. The first electrode 207 and the second electrode 307 may be respectively connected to a first voltage supply line 260 and a second voltage supply line 360. The first voltage supply line 260 and the second voltage supply line 360 may receive voltages from a first electrode pad 255 and a second electrode pad 355, respectively, and transmit the received voltages to the first electrode 207 and the second electrode 307, respectively. Therefore, the density of an electric field generated by the first electrode 207 and the second electrode 307 may be increased, thereby enhancing electron and hole transport efficiency.

Hereinafter, DNA chips according to ninth through fourteenth embodiments of the present invention will be described with reference to FIGS. 16 through 24. In the following embodiments of the present invention, the same constitutional elements as those in the previous embodiments may be represented by similar reference numerals and a description thereof may be omitted or simply provided. Constitutional elements different from those in the previous embodiments will be described in detail.

Figure 16:
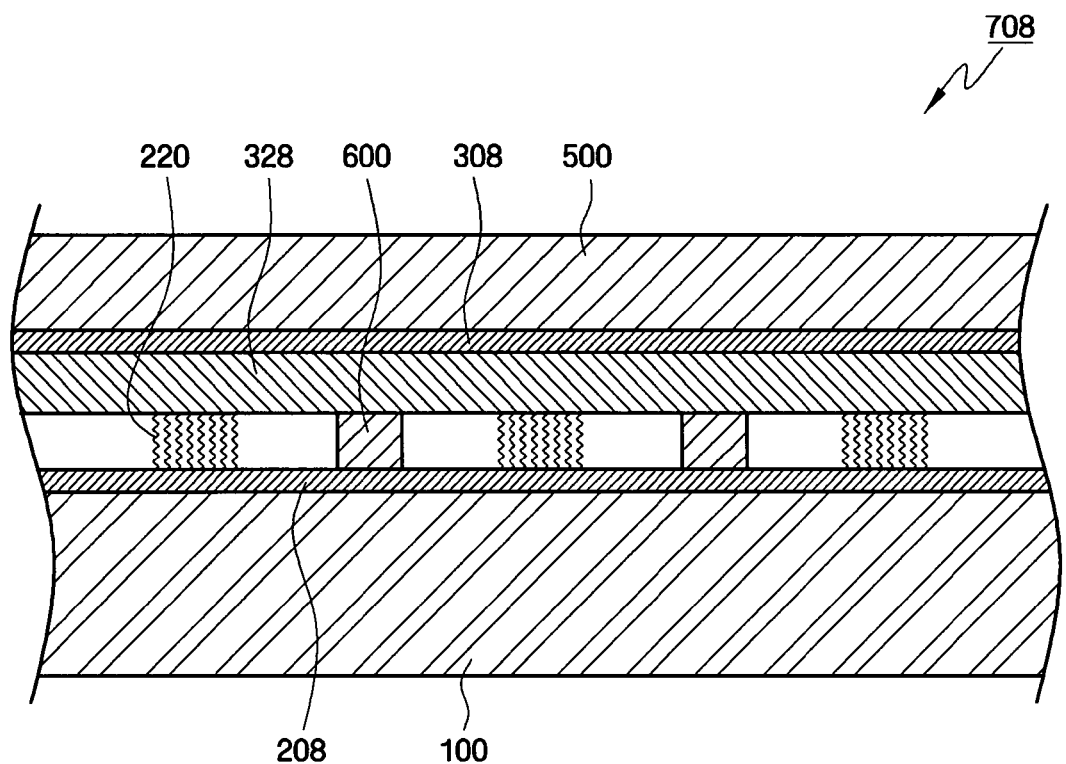
FIG. 16 illustrates a sectional view of a DNA chip according to a ninth embodiment of the present invention.

FIG. 16 illustrates a plan view of a DNA chip according to a ninth embodiment of the present invention. Referring to FIG. 16, a DNA chip 708 may include a first substrate 100 and a second substrate 500 facing each other.

The first substrate 100 may be substantially the same as substrates as described above with reference to FIGS. 1 through 3, and thus may be represented by the same reference numeral. A first electrode 208 may be formed on the first substrate 100. The first electrode 208 may be formed as a layer on the entire surface of the first substrate 100 irrespective of active regions. Reactive functional groups capable of reacting with monomers for oligonucleotide synthesis may be present in active regions of the first electrode 208. The reactive functional groups may be coupled to one ends of oligonucleotide probes 220.

The second substrate 500 may be opposite to the first substrate 100 and may be the same as or similar to the first substrate 100. However, taking into consideration that detection of light emission is performed in DNA analysis, at least one of the first substrate 100 and the second substrate 500 may be a transparent substrate. A second electrode 308 may be formed on a lower surface of the second substrate 500. The second electrode 308 may also be formed as a layer irrespective of the active regions. A lower surface of the second electrode 308 may be covered with a charge-carrier transport layer 328. A lower surface of the charge-carrier transport layer 328 may contact with or be adjacent to the distal ends of the oligonucleotide probes 220 from the first electrode 208.

At least one spacer 600 may be disposed between the first electrode 208 and the charge-carrier transport layer 328. The spacers 600 may serve to prevent the first substrate 100 and the second substrate 500 from being compressed and deformed, and the spacers 600 may provide a space for target supply to the oligonucleotide probes 220 of the active regions upon DNA analysis. The spacers 600 may be positioned in any region except the active regions, and the number and size of the spacers 600 may be widely varied.

Although not shown, the DNA chip 708 may further include an inlet and an outlet for injection and discharge of targets, since the oligonucleotide probes 220 may be sandwiched between the first substrate 100 and the second substrate 500. The inlet and the outlet may be formed at side portions of the DNA chip 708, or alternatively, may be bored through the first substrate 100 or the second substrate 500.

Figure 17:
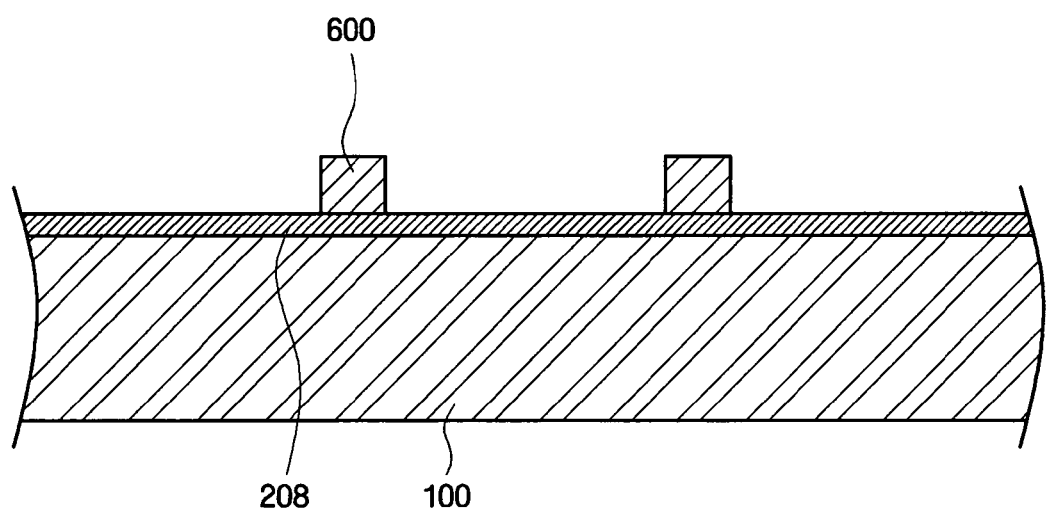
FIGS. 17 through 19 illustrate sequential sectional views of stages of a method of manufacturing the DNA chip according to the ninth embodiment of the present invention.
Figure 18:
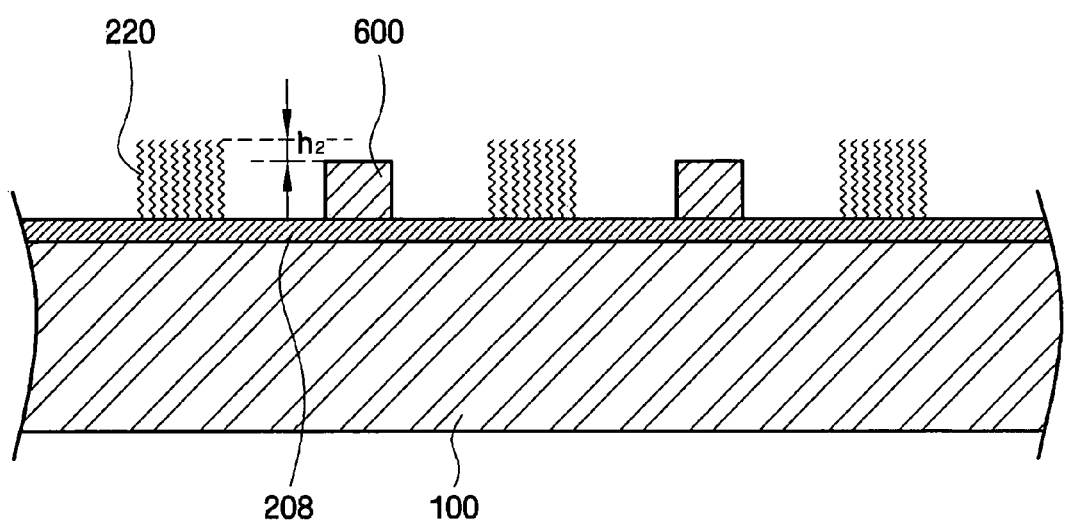
Figure 19:
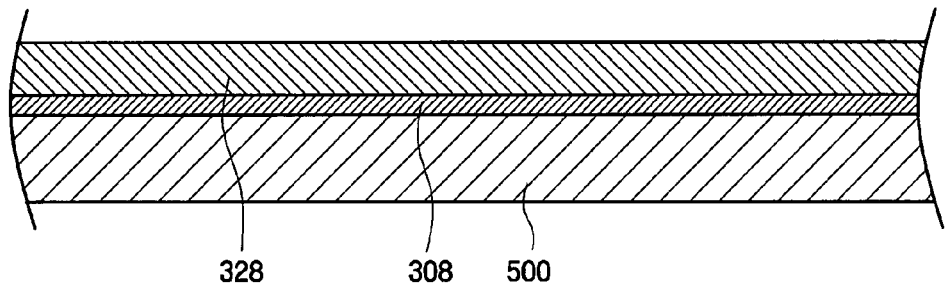

Hereafter, stages of a method of manufacturing the DNA chip according to the ninth embodiment of the present invention will be described. FIGS. 17 through 19 illustrate sequential sectional views of stages of a method of manufacturing the DNA chip according to the ninth embodiment of the present invention.

First, referring to FIG. 17, a first electrode 208 may be formed on a first substrate 100, and at least one spacer 600 may be formed on the first electrode 208. The spacers 600 may be formed by depositing a spacer forming material on the first electrode 208 followed by patterning using, e.g., photolithography.

Next, referring to FIG. 18, together with FIG. 17, active regions may be defined on the first electrode 208. This process may be similar to the active region formation described above with reference to FIG. 6, and a description thereof is omitted. Then, oligonucleotide probes 220 may be synthesized in the active regions. The oligonucleotide probes 220 may have a length sufficient to guarantee a reliable contact of the oligonucleotide probes 220 with a charge-carrier transport layer during a subsequent assembly between the first substrate 100 and a second substrate. The length of the oligonucleotide probes 220 may be greater than the height of the spacers 600 by a predetermined height $h_2$. Alternatively, after the length of the oligonucleotide probes 220 is determined, the spacers 600 may be formed considering the length of the oligonucleotide probes 220.

Next, referring to FIG. 19, a second electrode 308 and a charge-carrier transport layer 328 may be formed on a second substrate 500.

Referring to FIGS. 18 and 19, the first substrate 100 and the second substrate 500 may be disposed to face with each other and then joined together. As a result, a DNA chip as illustrated in FIG. 16 may be completed.

As a modification of the current embodiment of the present invention, previously synthesized oligonucleotide probes may directly spotted or printed on a first electrode instead of synthesizing oligonucleotide probes using, e.g., photolithography.

Figure 20:
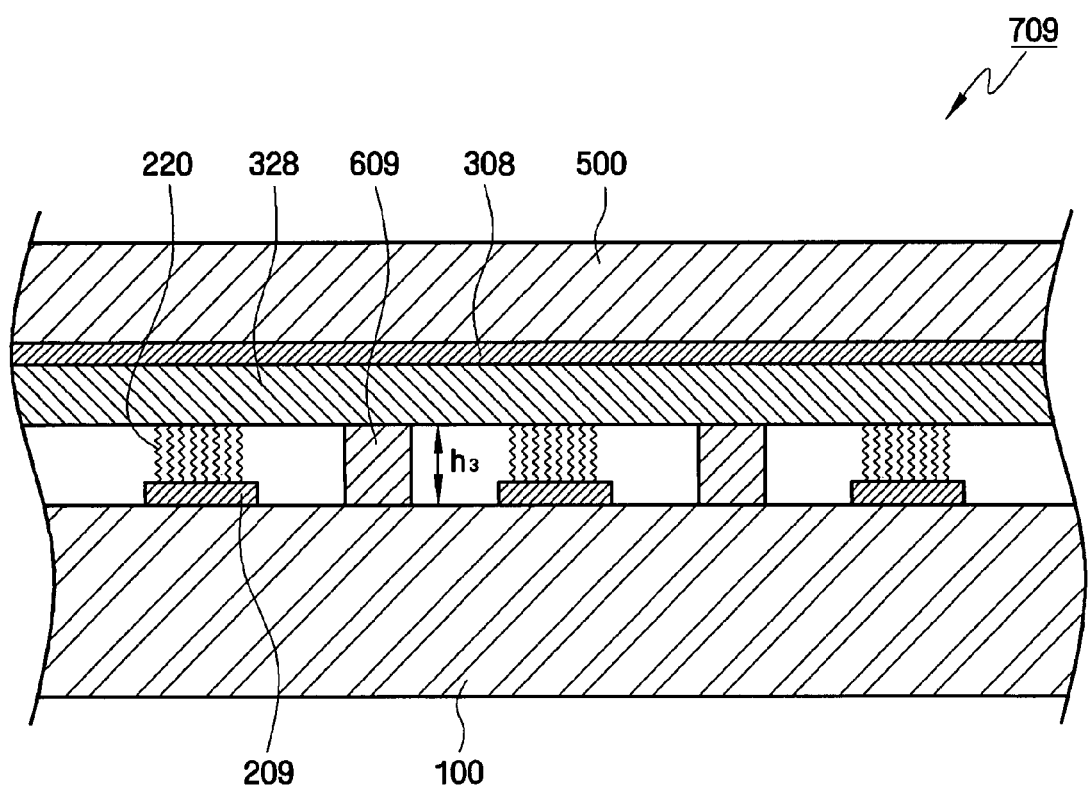
FIG. 20 illustrates a sectional view of a DNA chip according to a tenth embodiment of the present invention.

FIG. 20 illustrates a plan view of a DNA chip according to a tenth embodiment of the present invention. Referring to FIG. 20, a DNA chip 709 may include a first electrode 209 patterned into multiple first electrode patterns separated to respectively correspond to active regions. At least one spacer 609 may be disposed between a first substrate 100 and a charge-carrier transport layer 328. Thus, a height $h_3$ of the spacers 609 may be higher than that of the spacers 600 illustrated in FIG. 16 by a thickness of the first electrode 209. Oligonucleotide probes 220 may contact the patterned first electrode 209. The second electrode 308 may be on a second substrate 500.

Figure 21:
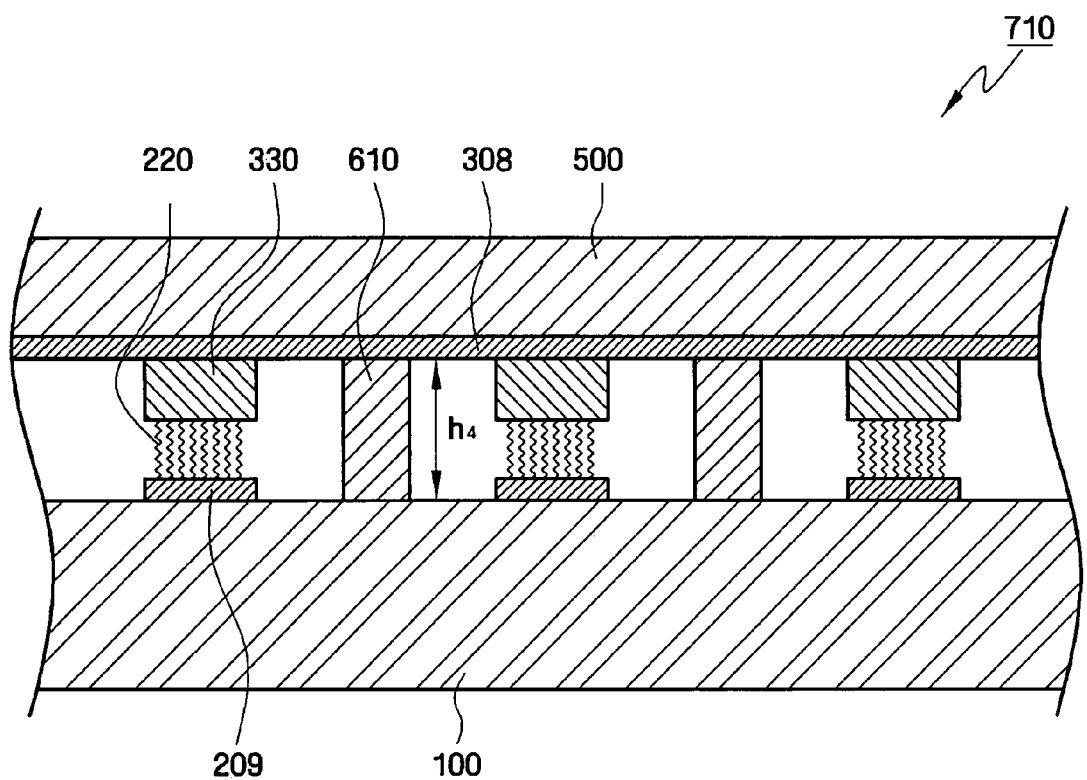
FIG. 21 illustrates a sectional view of a DNA chip according to an eleventh embodiment of the present invention.

FIG. 21 illustrates a plan view of a DNA chip according to an eleventh embodiment of the present invention. Referring to FIG. 21 a DNA chip 710 may include a charge-carrier transport layer 330 that may be patterned into multiple charge-carrier transport layer patterns separated to respectively correspond to active regions in which the oligonucleotide probes 220 will be formed on a patterned first electrode 209. At least one spacer 610 may be disposed between a first substrate 100 and a second electrode 308 on second substrate 500. Thus, a height $h_4$ of the spacers 610 may be higher than that of the spacers 609 illustrated in FIG. 20 by a thickness of the charge-carrier transport layer 330.

Figure 22:
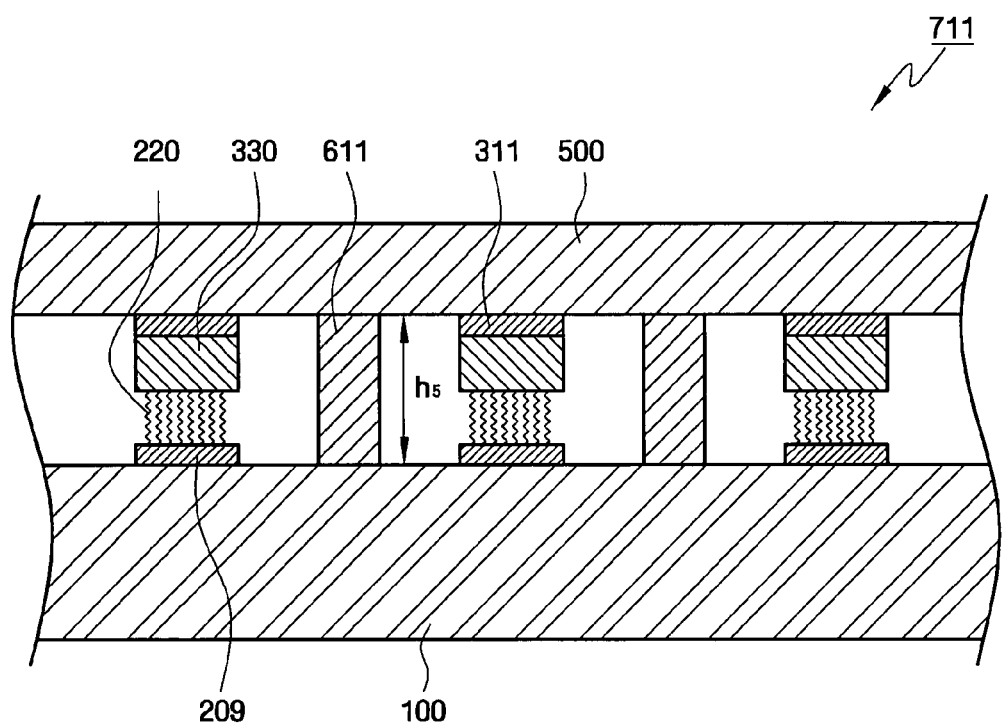
FIG. 22 illustrates a sectional view of a DNA chip according to a twelfth embodiment of the present invention.

FIG. 22 illustrates a plan view of a DNA chip according to a twelfth embodiment of the present invention. Referring to FIG. 22, a DNA chip 711 may include a second electrode 311 patterned into multiple second electrode patterns separated to respectively correspond to active regions that may contain the oligonucleotide probes 220. At least one spacer 611 may be disposed between a first substrate 100 and a second substrate 500. Thus, a height $h_5$ of the spacers 611 may be higher than that of the spacers 610 illustrated in FIG. 21 by a thickness of the second electrode 311.

According to the DNA chips of the tenth through twelfth embodiments of the present invention, electron/hole transport and electric-field generation may occur intensively in active regions, thereby enhancing emission efficiency.

Figure 23:
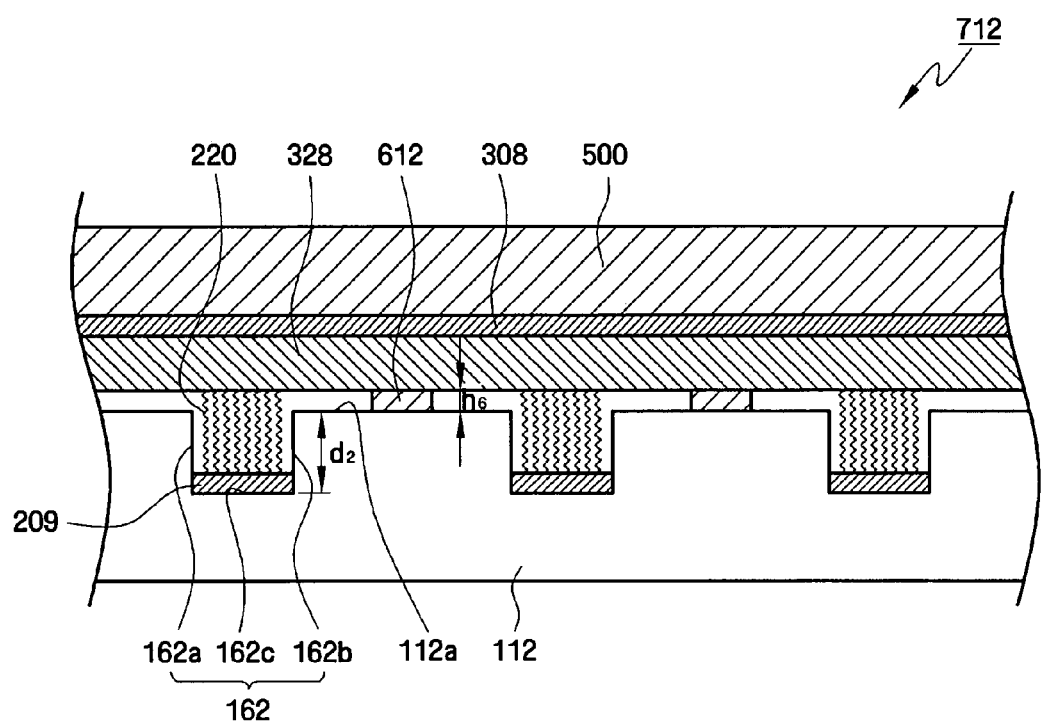
FIG. 23 illustrates a sectional view of a DNA chip according to a thirteenth embodiment of the present invention.

FIG. 23 illustrates a plan view of a DNA chip according to a thirteenth embodiment of the present invention. Referring to FIG. 23, a DNA chip 712 may include a trench 162 that may be depressed to a predetermined depth $d_2$ from an upper surface 112a of a first substrate 112. The trench 162 may include a bottom 162c and sidewalls 162a and 162b. A first electrode 209 may be immobilized with oligonucleotide probes 220 being formed on the bottom 162c of the trench 162. The height $h_6$ of a spacer 612 may be the same as a gap between the upper surface 112a of the first substrate 112 and a charge-carrier transport layer 328. A second electrode 308 may be on a second substrate 500. In the DNA chip 712, the first electrode 209 and the oligonucleotide probes 220 may be predominantly disposed in the trench 162, and it thus may be possible to reduce the thickness of the DNA chip 712 and to stably protect the oligonucleotide probes 220.

Figure 24:
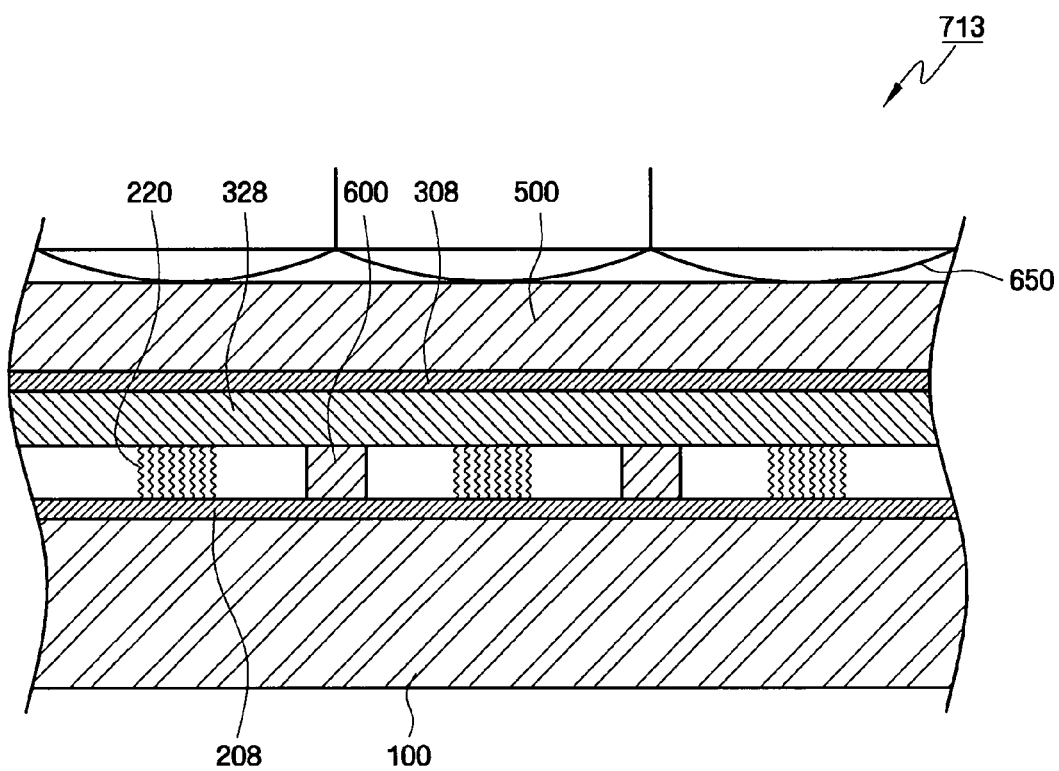
FIG. 24 illustrates a sectional view of a DNA chip according to a fourteenth embodiment of the present invention.

FIG. 24 illustrates a plan view of a DNA chip according to a fourteenth embodiment of the present invention. Referring to FIG. 24, a DNA chip 713 according to a fourteenth embodiment of the present invention is substantially the same as the DNA chip of the ninth embodiment of the present invention (see FIG. 16) except that a photodetector 650 may be formed on a second substrate 500. In this case, the second substrate 500 may be a transparent substrate. The photodetector 650 may be formed integrally with the second substrate 500 or a first substrate 100, or the photodetector 650 may be attached detachably to either the second substrate 500 or the first substrate 100. The photodetector 650 may be, e.g., CCD, CIS, etc. The DNA chip 713 may be advantageous to obtain more rapid DNA analysis after target-probe hybridization.

Figure 25:
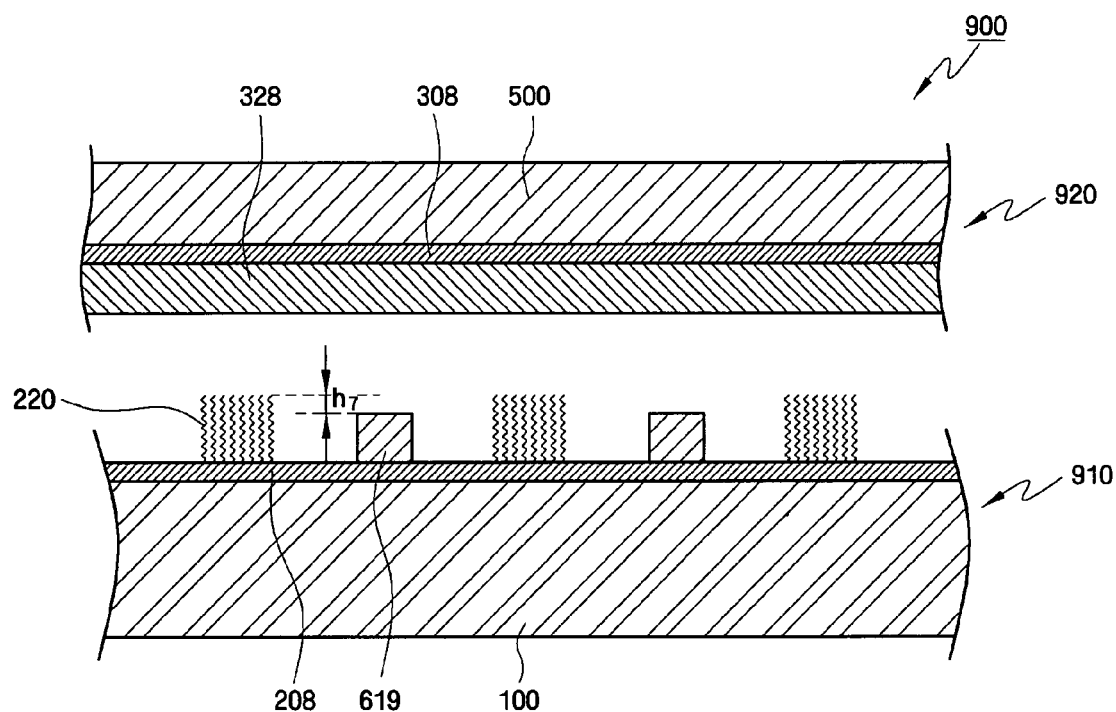
FIG. 25 illustrates a sectional view of a DNA chip kit according to an embodiment of the present invention.

Hereinafter, a DNA chip kit according to an embodiment of the present invention will be described. FIG. 25 illustrates a sectional view of a DNA chip kit according to an embodiment of the present invention.

Referring to FIG. 25, a DNA chip kit 900 may includes a first unit 910 including a first substrate 100 and a second unit 920 including a second substrate 500.

With respect to the first unit 910, a first electrode 208 may be formed as a layer on the entire surface of the first substrate 100 irrespective of active regions. Reactive functional groups capable of reacting with monomers for oligonucleotide synthesis may be present in the active regions of the first electrode 208. The reactive functional groups, when activated, may be coupled to one of the ends of oligonucleotide probes 220. The first unit 910 may further include at least one spacer 619. The height of the spacers 619 may be lower than the length of the oligonucleotide probes 220 by a predetermined height $h_7$ in order to guarantee a contact margin between the distal ends of the oligonucleotide probes 220 from the first electrode 208 and a charge-carrier transport layer 328 of the second unit 920.

With respect to the second unit 920, the second electrode 308 and the charge-carrier transport layer 328 may sequentially be on the second substrate 500.

Although not shown in FIG. 25, the DNA chip kit 900 may further include, as a third unit, an organic light-emitting material capable of binding with the oligonucleotide probes 220. The organic light-emitting material may be as described above with reference to FIG. 4.

The DNA chip kit 900 may have substantially the same structure as the DNA chip according to the ninth embodiment of the present invention (see FIG. 16) except that a first substrate structure, i.e., the first unit 910, and a second substrate structure, i.e., the second unit 920, may be separated from each other. When performing DNA analysis using the DNA chip kit 900, it may be easy to perform target supply to the first unit 910 since an upper portion of the first unit 910 is opened, and an additional inlet and outlet may not be required. After target supply to the first unit 910 is performed for the purpose of target-probe hybridization, the second unit 920 and the first unit 910 may be joined together and a voltage may be applied.

The DNA chip kit 900 may serve as an example of a DNA chip kit manufactured by dividing the DNA chip of FIG. 16 into two substrate units. Of course, the DNA chips illustrated in FIGS. 17 through 24 may also serve as DNA chip kits by dividing each of the DNA chips into two substrate units.

The above-described embodiments may be optionally combined. According to a combination between the embodiment illustrated in FIG. 11 and the embodiment illustrated in FIG. 13, after a barrier rib pattern is formed on a substrate, a second electrode and a charge-carrier transport layer formed in a trench may extend to a sidewall of the barrier rib pattern formed on the substrate.

As described above, according to a DNA chip of the present invention, DNA analysis may be performed by detecting light emitted from an organic light-emitting material using an electrical method, and noise due to external light or reflected light may not result. Therefore, more precise DNA analysis may be achieved, thereby increasing the reliability of DNA analysis.

Exemplary embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A DNA chip, comprising:
   a substrate;
   at least one first electrode and at least one second electrode on the substrate, the first electrode and the second electrode being opposite to and separate from each other;
   a plurality of oligonucleotide probes, one end of the oligonucleotide probes being immobilized on the first electrode; and
   a charge-carrier transport layer on the second electrode, the charge-carrier transport layer contacting an other end of the oligonucleotide probes.

2. The DNA chip as claimed in claim 1, wherein the oligonucleotide probes are immobilized on an inner sidewall of the first electrode facing the second electrode, and the charge-carrier transport layer is on an inner sidewall of the second electrode facing the first electrode.

3. The DNA chip as claimed in claim 2, wherein the substrate includes a trench, and the first electrode and the second electrode are respectively on two opposite sidewalls of the trench.

4. The DNA chip as claimed in claim 2, further comprising a barrier rib pattern contacting with outer sidewalls of at least one of the first electrode and the second electrode.

5. The DNA chip as claimed in claim 2, wherein the second electrode is inclined so that a lower portion of the second electrode is closer to the first electrode.

6. The DNA chip as claimed in claim 1, wherein the first electrode includes a reactive functional group that can react with monomers for synthesis of the oligonucleotide probes at or on a surface of the first electrode.

7. A DNA chip, comprising:
   a first substrate having a first electrode and a plurality of oligonucleotide probes, one end of the oligonucleotide probes being immobilized on the first electrode; and
   a second substrate having a second electrode and a charge-carrier transport layer, the first substrate and the second substrate being opposite to each other so that the charge-carrier transport layer contacts an other end of the oligonucleotide probes.

8. The DNA chip as claimed in claim 7, wherein the first electrode includes a plurality of first electrode patterns.

9. The DNA chip as claimed in claim 8, wherein the first substrate includes at least one trench, and the first electrode is on a bottom of the trench.

10. The DNA chip as claimed in claim 7, wherein the charge-carrier transport layer includes a plurality of charge-carrier transport layer patterns.

11. The DNA chip as claimed in claim 7, wherein the first electrode includes a functional group that reacts with monomers for synthesis of the oligonucleotide probes at or on a surface of the first electrode.

12. The DNA chip as claimed in claim 7, further comprising a spacer between the first electrode and the second electrode.

13. The DNA chip as claimed in claim 7, further comprising a photodetector attached to the first substrate or the second substrate.

14. A DNA chip kit, comprising:
   a first unit including a first substrate, a first electrode on the first substrate, and a plurality of oligonucleotide probes, one end of the oligonucleotide probes being immobilized on the first electrode; and a second unit including a second substrate, a second electrode on the second substrate, and a charge-carrier transport layer on the second electrode, the charge-carrier transport layer being capable of contacting an other end of the oligonucleotide probes.

15. The DNA chip kit as claimed in claim 14, wherein the first electrode includes a plurality of respectively separated first electrode patterns.

16. The DNA chip kit as claimed in claim 15, wherein the first substrate includes at least one trench, and the first electrode is on a bottom of the trench.

17. The DNA chip kit as claimed in claim 14, wherein the charge-carrier transport layer includes a plurality of charge-carrier transport layer patterns.

18. The DNA chip kit as claimed in claim 14, wherein the first electrode includes a reactive functional group that reacts with monomers for synthesis of the oligonucleotide probes at or on a surface of the first electrode.

19. The DNA chip kit as claimed in claim 14, further comprising a light-emitting material of targets binding with the oligonucleotide probes.

20. The DNA chip kit as claimed in claim 14, further comprising a photodetector attached to the first substrate or the second substrate.

21. A method of manufacturing a DNA chip, comprising:

forming at least one first electrode and at least one second electrode on at least one substrate, the first electrode and the second electrode being opposite to and separated from each other;

forming a charge-carrier transport layer on the second electrode; and immobilizing a plurality of oligonucleotide probes on the first electrode, one end of the oligonucleotide probes contacting the first electrode and the other end of the oligonucleotide probes contacting the charge-carrier transport layer.

* * * * *